(12) United States Patent
Wei et al.

(10) Patent No.: US 6,582,734 B1
(45) Date of Patent: Jun. 24, 2003

(54) ANTIMICROBIAL COMPOSITION USEFUL FOR THE TREATMENT OF BOVINE MASTITIS

(75) Inventors: Guang-jong Jason Wei, Mendota Heights, MN (US); David Daniel McSherry, Minneapolis, MN (US); Francis Lawrence Richter, Lino Lakes, MN (US); Richard K. Staub, Lakeville, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 09/619,788

(22) Filed: Jul. 20, 2000

(51) Int. Cl.⁷ .................. A01N 25/24; A01N 37/00; A01N 59/00; A01N 59/08; A61K 37/20
(52) U.S. Cl. .................. 424/665; 424/405; 424/407; 424/409; 424/465; 424/468; 424/489; 424/661; 514/553; 514/557; 514/558; 514/560
(58) Field of Search .................. 424/407, 661, 424/665, 405, 409, 465, 468, 489; 514/553, 557, 558, 560

(56) References Cited

U.S. PATENT DOCUMENTS

| | | | |
|---|---|---|---|
| 2,022,262 A | 11/1935 | White | 87/5 |
| 2,071,091 A | 2/1937 | Taylor | 167/17 |
| 2,071,094 A | 2/1937 | Vincent | 167/17 |
| 4,084,747 A | 4/1978 | Alliger | 239/4 |
| 4,330,531 A | 5/1982 | Alliger | 424/149 |
| RE31,779 E | 12/1984 | Alliger | 252/187.23 |
| 4,585,482 A | 4/1986 | Tice et al. | 106/15.05 |
| 4,891,216 A | 1/1990 | Kross et al. | 424/78 |
| 4,986,990 A | 1/1991 | Davidson et al. | 424/665 |
| 5,009,875 A | 4/1991 | Kelley et al. | 423/477 |
| 5,185,161 A | 2/1993 | Davidson et al. | 424/665 |
| 5,252,343 A | 10/1993 | Kross | 424/661 |
| 5,368,868 A | 11/1994 | Winicov | 424/667 |
| 5,407,656 A | 4/1995 | Roozdar | 423/477 |
| 5,631,300 A | 5/1997 | Wellinghoff | 514/772.3 |
| 5,651,977 A | 7/1997 | Kross | 424/419 |
| 5,695,814 A | 12/1997 | Wellinghoff et al. | 427/213 |
| 5,707,739 A | 1/1998 | Wellinghoff et al. | 428/403 |
| 5,820,822 A | 10/1998 | Kross | 422/37 |
| 5,853,689 A | 12/1998 | Klatte | 423/478 |
| 5,922,776 A | 7/1999 | Wellinghoff et al. | 514/772.3 |

FOREIGN PATENT DOCUMENTS

| | | |
|---|---|---|
| EP | 0 906 724 A1 | 4/1999 |
| WO | WO 98/38865 | 9/1998 |
| WO | 99/16418 * | 4/1999 |
| WO | 99/24356 | 5/1999 |
| WO | 00/13506 | 3/2000 |

OTHER PUBLICATIONS

Derwent Pub. Ltd. JP60127201 abstract, Jul. 6, 1985.

* cited by examiner

*Primary Examiner*—John Pak
(74) *Attorney, Agent, or Firm*—Vidas, Arrett & Steinkrau

(57) ABSTRACT

The present invention relates to a two-part antimicrobial composition comprising at least one chlorine dioxide generating component comprising at least one metal chlorite and at least one acid-forming compound in a solid carrier, and at least one liquid aqueous component. The composition further comprises at least one antimicrobial fatty acid having from about 2 to about 15 carbon atoms, and preferably from about 6 to about 12 carbon atoms. The components, upon mixing, form a composition having a pH in the range of about 5 to about 10.

18 Claims, No Drawings

ANTIMICROBIAL COMPOSITION USEFUL FOR THE TREATMENT OF BOVINE MASTITIS

FIELD OF THE INVENTION

The present invention relates to a two-part antimicrobial composition comprising at least one chlorine dioxide generating component comprising at least one metal chlorite and at least one acid-forming compound in a solid carrier, and at least one liquid aqueous component. The composition further comprises at least one antimicrobial fatty acid having from about 2 to about 15 carbon atoms, and preferably from about 6 to about 12 carbon atoms. The components, upon mixing, form a composition having a pH in the range of about 5 to about 10, and preferably from about 5.2 to about 8.

BACKGROUND OF THE INVENTION

Bacterial infection, particularly bovine mastitis, is the most costly and difficult problem that a dairy herdsman will typically have to deal with.

Mastitis is an inflammation of the mammary gland that occurs primarily as a result of a bacterial infection that gains entry into the udder of the mammal via the teat canal. Mastitis decreases the cow's milk production and reduces the quality of the milk. In more severe cases of mastitis, the milk will have to be discarded, and if the disease resists treatment, the cow may have to be destroyed. A further problem is that a mastitis infection can spread from cow to cow.

Mastitis can occur in two forms that are referred to as clinical and subclinical mastitis. Both decrease milk production, but the milk must be discarded if the cow has clinical mastitis, and in untreatable cases, as stated above, the cow may have to be destroyed. In the case of the clinical disease, attempts at treatment have involved infusion of an antibiotic into the udder of the animal.

There are numerous organisms that cause mastitis, but the most common are *streptococcus agalactiae* and *staphylococcus aureus*. Other environmental and contagious microorganisms that cause this disease include coliforms, *Klebsiella pneumoniae, Actinomyces pyogenes, Corynebacterium bovis, Listeria monocytogenes, Pseudomonas aeruginosa, Mycoplasma bovis*, as well as other species of staph and strep. Treatment is generally started before the species causing the disease is identified, and it is therefore desirable to have an antibiotic that has the greatest efficacy, and that acts on as many species that cause the disease as possible. These microorganisms lurking in the surrounding environment such as plants and bedding (i.e. straw, hay, grass, wood shavings and the like), feces, soil, water, feed, and so forth are opportunistic and are spread from cow to cow during the milking process. The entrance of the microorganism is through the teat orifice and teat canal of the animal.

Dairy herd management focuses on both the treatment and prevention of mastitis infections. As stated above, treatment typically involves infusion of antibiotics into the udder of the infected cow(s), and prevention involves routine hygienic practices. Routine hygienic practices used for the prevention of mastitis (as well as preventing spreading of the disease) involves treating (i.e. dipping) the teats of the udder of a cow immediately after each milking period with an antiseptic "teat dip." This has become a standard practice for dairy herdsmen as it has been proven to be a very effective way to prevent intramammary mastitis in cows.

Teat dips may be divided into several general categories including "predip" teat dips that are used to clean the udder of the cow prior to milking, "prepost" teat dips that are applied to the udder of the cow after milking, and "barrier" teat dips that are also applied to the udder after milking and are further designed to remain on the udder of the cow in between the milking periods.

Mastitis causing microorganisms are found in both the barn in which the cow is milked and in the environment the cow enters in between the milking periods. Prepost teat dips are designed to work on those microorganisms that are found in the barn, and that are spread from cow to cow during the milking period.

The barrier teat dips are designed to remain on the cow during the nonmilking periods. Barrier teat dips therefore comprise a film-forming agent that allows the teat dip to form a barrier or phophylaxis over the teats of the cow in order to prevent entrance of microorganisms through the teat orifice from the surrounding environment in the nonmilking periods. These barrier teat dips may or may not contain an antimicrobial agent, although in recent years it has become increasingly popular that the barrier teat dips have both film-forming characteristics and antimicrobial activity because some of the mastitis causing microorganisms have been known to penetrate the barrier and migrate into the teat canal.

There now exists a variety of commercially available predip, prepost and barrier teat dips, including those based on iodophors (i.e. iodine), quaternary ammonium compounds, chlorhexidine salts, chlorine release compounds such as alkali hypochlorites; oxidizing compounds such as hydrogen peroxide and peracids; protonated carboxylic acids (i.e. fatty acids) such as heptanoic, octanoic, nonanoic, decanoic, undecanoic, and so forth; acid anionics such as alkylaryl sulfonic acids; chlorine dioxide; and so forth. Such compositions have varying degrees of effectiveness.

Chlorine dioxide has been found to be an extremely effective chemical for use as an antimicrobial and over several decades has found increasing popularity for disinfecting, sanitizing, sterilizing, deodorizing, and so forth. Further, this chemical has been found to be quite useful in the prevention and treatment of bovine mastitis. This compound is typically generated in solution (i.e. aqueous medium) by mixing a metal chlorite salt with a strong mineral acid or a large amount of a strong organic acid. The stability of such solutions is an issue, however, and mixing of the acid and the metal chlorite salt is not recommended until just prior to use.

A variety of approaches have been taken for using chlorine dioxide. Such approaches are found in U.S. Pat. No. 4,084,747 and its reissue Re. Pat. No. 31,779; U.S. Pat. Nos. 4,585,482; 4,986,990 and 5,185,161; 4,891,216 and 5,651,977; and 5,820,822.

Various problems have been encountered with teat dips that utilize chlorine dioxide generating components. One such problem has been the low pH typically required for sufficient generation of chlorine dioxide. For antimicrobial compositions used on either human or mammalian skin, an acidic pH is of concern due to the irritation caused to tissue. Another problem associated with chlorine dioxide generation is the shelf life. Once chlorine dioxide generation is initiated, the compositions begin to lose efficacy and must typically be used in a matter of days There remains a need in the art for a simple, yet effective and long-lasting antimicrobial system based on chlorine dioxide, and that may be used for such applications as the prevention and treatment of mastitis.

SUMMARY OF THE INVENTION

The present invention relates to a novel and improved two-part antimicrobial composition having longer lasting efficacy against microbes, and is useful as a teat dip comprising at least one chlorine dioxide generating component in a solid carrier and at least one liquid aqueous component. The chlorine dioxide generating component has at least one metal chlorite and at least one acid-forming compound. The acid-forming compound is preferably a protic acid, but includes any type of acid-forming compound. It is necessary that the acid-forming compound have a pKa of less than that of the fatty acid. Chlorine dioxide will not be adequately generated at a pH of about 5–10.

The antimicrobial composition further comprises at least one antimicrobial fatty acid which may be supplied in the solid component, but is preferably supplied in solution in the aqueous component. The fatty acid is characterized as having from about 2 to about 15 carbon atoms, and preferably from about 6 to about 12 carbon atoms. The fatty acid has a pKa of about 5.

The solid component is permeable to water in liquid form, or is sensitive to or dissolvable in water in liquid form. Upon mixing of the components, chlorine dioxide is generated.

The resultant mixed composition has a pH in the range of about 5 to about 10, preferably from about 5 to about 8, and most preferably from about 5.5 to about 8.

The composition has improved antimicrobial effectiveness in that the chlorine dioxide acts immediately to kill microorganisms that cause mastitis, while the fatty acid remains antimicrobially active over a longer period against the mastitis causing microorganisms.

Furthermore, the composition is effectively antimicrobial at a relatively neutral pH of about 5 to about 10, preferably about 5.5 to about 10, and most preferably from about 5.5 to about 8, which results in less problems with irritation to the skin.

The compositions of the present invention may be utilized as predip and prepost teat dips, as well as barrier teat dips upon the addition of a film-forming agent.

The compositions of the present invention further have the benefit that they are simple and easy to use.

DETAILED DESCRIPTIONS OF THE PREFERRED EMBODIMENTS

The present invention relates to a two-part antimicrobial composition. The first part comprises at least one acid-forming compound and at least one metal chlorite in a solid form, and the second part is an aqueous based solution. The first part may be referred to as the chlorine dioxide generating component. A fatty acid is further provided in the composition in either the first part as a solid, or in the second part as a solution. Preferably, the antimicrobial fatty acid is provided in aqueous solution.

The addition of the fatty acid to the resultant composition, provides the composition with residual, longer-lasting antimicrobial activity. The two parts are blended prior to use, and are particularly useful as a teat dip composition. The first component generates chlorine dioxide, an effective antimicrobial agent, in the presence of the second, aqueous based part.

The chlorine dioxide generating compounds useful herein include metal chlorites. Preferred metal chlorites are water soluble and include alkaline earth metal chlorites and alkali metal chlorites such as potassium chlorite and sodium chlorite. Alkaline earth metal chlorites include barium chlorite, calcium chlorite and magnesium chlorite. Sodium chlorite is a particularly preferred compound. The metal chlorite is preferably provided in a powder (i.e. salt) form. The metal chlorite is preferably present in the resultant antimicrobial formulation at a concentration of about 0.01% to about 20% by weight, and preferably from about 1.0% to about 14%. However, the amount of metal chlorite selected is dependent on the amount of chlorine dioxide generation that is desired.

Consequently, the metal chlorite is added at a concentration sufficient to generate from about 1 to about 500 ppm chlorine dioxide, preferably from about 20 to about 500 ppm chlorine dioxide, and most preferably from about 100 to about 400 ppm chlorine dioxide. For a teat dip, the amount of chlorine dioxide present depends on the amount of organic soil present at the time of use (10% milk will raise the amount of chlorine dioxide required substantially because protein reacts rapidly with $ClO_2$). As an example, in the absence of organic soil, as little as a few ppm of chlorine dioxide is required for an effective microbial kill. However, in the presence of organic soil, an initial amount of about 200 to about 500 ppm of chlorine dioxide is needed, and preferably from about 250 to about 400 ppm of chlorine dioxide.

For hard surface sanitizing applications, the soil demand is not as high and the amount of chlorine dioxide required is substantially less. For example, the amount of chlorine dioxide required may be about 1 to about 50 ppm and preferably about 2 to about 20 ppm.

The acid-forming compounds useful herein include water sensitive or soluble compounds, as well as substantially water-insoluble acid-forming compounds. The acid-forming material is preferably a solid material, and is preferably hydrophilic. The acid-forming compound does not react to any substantial degree with the metal chlorite in the absence of water. The acid-forming compound may itself be protic, or it may produce protons upon contact with water and the metal chlorite. The pKa of the acid-forming compound is less than that of the antimicrobial fatty acid. Antimicrobial fatty acids have a pKa of about 5, typically they are about 4.8. The acid-forming compound consequently has a pKa of less than 4.8, and is preferably 4.0 or less, more preferably about 3.0 or less and even more preferably about 2.0 or less. It is necessary that the acid-forming compound form a localized low pH. The generation of chlorine dioxide will not be adequate at a pH that is close to neutral, or is basic. The pH required in order to produce chlorine dioxide is lower and consequently, the pH of the solution at the point of reaction between the metal chlorite and the acid-forming compound is lower than that of the solution generally.

The acid-forming compounds useful to the present invention are vast in number and include protic acids, non-protic acids, acidic salts, mineral acids, as well as other types of acid-forming compounds, some discussed in more detail below. A primary requirement is that the acid-forming compound be able to generate protons in water.

The acid-forming compounds useful herein include protic acids. Some useful protic acids include carboxylic acids and dicarboxylic acids such as aromatic carboxylic acids, α-hydroxy carboxylic acids, β-hydroxy carboxylic acids, unsaturated carboxylic acids, and so on and so forth. Some specific acids useful herein include but are not limited to benzoic, boric, citric, fumaric, oxalic, tartaric acid, lactic acid, maleic acid, and so forth. The acid-forming compound may also be the anhydride of these protic acids, for instance, maleic anhydride. Preferably, the protic acids are used in the present invention in amounts of about 0.1% to about 5%, and preferably about 0.1% to about 1% by weight of the total antimicrobial composition.

Other acid-forming compounds include water soluble acid salts of calcium, magnesium, barium, lithium, aluminum, sodium, potassium, and so forth. Such compounds include sulfuric and phosphoric acid salts, calcium chloride, magnesium chloride, magnesium nitrate, lithium chloride, magnesium sulfate, aluminum sulfate, sodium acid sulfate, sodium dihydrogen phosphate, potassium acid sulfate, potassium dihydrogen phosphate, and so forth, and mixtures thereof.

Useful mineral acids include sulfuric, hydrochloric, nitric and sulfamic acids.

Other acid-forming compounds include, but are not limited to, acids which are already included in a solid carrier such as synthetic molecular sieves including synthetic zeolite A, X and Y, mordenite and ZSM-5 which have both been converted to the substantially hydrogen ion ($H^+$) exchanged forms; natural zeolites such as chabazite and clinoptilolite; dealuminated zeolite Y; acid ion exchange resins such as Dowex® HCR-S resins available from the Dow Chemical Co. in Midland, Mich.; insoluble organic acid anhydrides such as phthalic anhydride; and so forth; and mixtures thereof.

Other acid-forming compounds are the clays including acid treated, calcined and hydrous clays, and so forth. Hydrous clays include bentonite, kaolin, attapulgite and halloysite. Calcined clays include spinel phase calcined kaolin, calcined bentonite, calcined halloysite and calcined attapulgite. Acid treated clays are such that the clays are contacted with acidic solutions containing sulfuric acid, hydrochloric acid, nitric acid or other acidic compounds such as lanthanum chloride and include acid treated metalkaolin, acid treated bentonite, acid treated attapulgite and acid treated halloysite.

Typically, the zeolites or clays are treated with acids such as sulfuric, nitric and hydrochloric acids.

Acid-forming compounds that find utility in the present invention are described in detail in WO 98/38865 and in WO 99/24356 both incorporated in their entirety by reference herein. The above list of acid-forming compounds is intended as illustrative, and not as an exclusive list of all the acid-forming compounds useful herein, and as such is not intended as a limitation on the scope of the present invention. One of skill in the art would know how to select such an acid-forming compound.

The amount of the acid-forming compound will depend on how much metal chlorite is present in the compositions. It is desirable to have an excess of acid-forming compound present. Higher rates of reaction require higher concentrations of acid-forming compounds. The concentration of acid required will also depend on the pKa and reactivity of the acid, however.

The amounts of the metal chlorite and the acid-forming component are selected so as to produce a quantity of chlorine dioxide that is sufficient for effective antimicrobial efficacy. Generally, the amount of chlorine dioxide generated in the resultant aqueous solution of the present invention will be from about 0.5 ppm to about 500 ppm, preferably from about 50 to about 450 ppm, and most preferably from about 100 to about 400 ppm.

The metal chlorite and the acid-forming compound of the present invention are included with a solid carrier. The solid carrier is a neutral compound, and may, for instance, be any clay of the aluminum silicate type including bentonite, kaolin, attapulgite, halloysite, polyorganosilicates, and so forth; micas; talcs; zeolites; and so forth.

The acid-forming compound may be found in either a solid or in a liquid form depending on the acid-forming compound utilized. If the acid is a solid, then the metal chlorite and the acid may be mixed together with the solid carrier at one time, for instance clay or zeolite, and supplied preferably in a pressed tablet form. In this instance, the solid carrier is utilized as a diluent in order to prevent the concentration of the metal chlorite and the acid from being undesirably high. At high concentrations the mix can become explosive.

Alternatively, the metal chlorite may be mixed with a solid carrier in solution, and then dried. Separately, the acid may be mixed with a solid carrier and then the subsequently, the two, now carried reactants, may be mixed together.

If, on the other hand, the acid is a liquid, it must be first mixed with a solid carrier so that the acid is now in solid form. In this instance, the metal chlorite, a solid itself, may be added to the acid/carrier mix, or the metal chlorite may be first mixed with a solid carrier itself, and then the metal chlorite/carrier component is mixed with the acid/carrier component. If the metal chlorite is first mixed with a carrier, it is done in solution and then dried prior to mixing with the acid/carrier mix.

Optionally, the fatty acid antimicrobial may be added to the metal chlorite and/or acid-forming compound at any point of the process.

The resultant mix may then be supplied to the end user in any solid form including powders, agglomerates, tablets, pellets, granules, capsules, and so forth. A preferable solid form is a tablet form. The reactants, i.e. the metal chlorite and the acid forming compound react in the presence of water so it is necessary to further package them in some form that will keep them substantially free from the presence of water, either in vapor form, or in liquid form. Otherwise, chlorine dioxide may be prematurely generated. Chlorine dioxide generation may also occur in the presence of water vapor, i.e. that absorbed from the ambient air. The reactants are therefore preferably packaged, transported and stored in a substantially moisture-proof package.

The packaging materials may be insoluble or soluble. Examples of insoluble materials include thermoplastic polymeric materials such as nonwoven polyethylene such as Tyvek® available from DuPont in Midland, Mich. and expanded polytetrafluoroethylene such as GoreTex® available from W. L. Gore.

Permeable membranes may be soluble, dissolvable or permeable and include gelatins, perforated materials such as perforated Tyvek®, and so forth.

Some packaging options include membranes, films, sachets, bags, pouches, capsules and so forth, that keeps the tablet free from moisture, but which degrades or dissolves in water, or is permeable to water in liquid form. These packages will allow for the controlled release of chlorine dioxide. In the case of a package that is permeable to water in liquid form, the package must be permeable to chlorine dioxide, and thereby finction by allowing water in, and chlorine dioxide out. Chlorine dioxide generation can be increased by increasing the water solubility of the package, or by increasing the water permeability of the package in which the solid is placed.

The use of membranes which allow the passage of water in liquid and/or vapor to pass into the membrane to the solid reactants from a liquid body of water and subsequently chlorine dioxide out of the membrane is discussed in WO 99/24356 herein incorporated by reference in its entirety.

The tablets may be removed from the package, and the package discarded. Tablets may also be packaged in composite type materials such as a polyolefin film over an aluminum foil.

In one specific embodiment of the present invention, the metal chlorite and the acid-forming compound are in a solid mixture that has been pressed into a tablet form. Optionally, the fatty acid antimicrobial agent may be added to the pressed powder tablet. The tablet is then packaged in a moisture proof barrier. The moisture-proof barrier may be comprised of any substantially water-insoluble thermoplastic material. Each tablet may be individually packaged, the package discarded once the tablet is removed, or several tablets may be packaged in a resealable container, such as those similar to a Zip-loc®, that will provide a moisture proof barrier. The tablet(s) is then added to a specified amount of the second part, i.e. the aqueous solution.

In another embodiment, the metal chlorite and the acid-forming compound are in a solid powder form and are supplied in a solid carrier such as a sachet, pouch, membrane, and so forth that is permeable to water in liquid form. If a sachet, pouch, or membrane is used, the metal chlorite and the acid-forming compound are separated from the rest of the components by the sachet, pound or membrane. In this embodiment, the solid carrier must also allow the passage of chlorine dioxide into the aqueous medium upon its generation. Further to this embodiment, the solid carrier may be divided into chambers that separate the acid-forming compound and the metal chlorite from one another to prevent a reaction should water in vapor form enter the solid carrier.

Optionally, the tablets or the powder, may be provided in a package or membrane that dissolves upon the addition to an aqueous medium, thereby allowing liquid water to penetrate and come into contact with its ingredients.

One example of a membrane material is gelatin. Gelatin is supplied in the form of a capsule under the tradename of Capsugel®, available from Warner Lambert in Morris Plains, N.J.

As stated above, the pH of the solution is about 5–10, preferably about 5.2 to about 10, preferably about 5.2 to about 8, and most preferably about 5.5 to about 8. Chlorine dioxide may not be adequately generated at such high pH's, however. It is therefore necessary that the acid-forming compound and the metal chlorite be in close proximity to one another, and that the pH at the local of the metal chlorite be lower than that of the solution generally. The pKa of the acid-forming compound is therefore quite low, i.e. 4.5 or less.

The present invention provides for the controlled release of chlorine dioxide by employing solid reactants that dissolve readily upon contact with water. The solid, e.g. a tablet, dissolves in the aqueous solution, the metal chlorite and the acid-forming compound react and chlorine dioxide is released. Close proximity of the reactants is desirable in order to effectively release chlorine dioxide at such a high pH.

These and other embodiments are envisioned by the present inventors. Furthermore, one of skill in the art will understand that combinations of these embodiments will also provide a controlled release of chlorine dioxide by preventing water actuation of the composition until it is so desired, as well as how quickly water will contact the reactants. Controlled chlorine dioxide generation is discussed in detail in WO 99/24356 incorporated by reference herein in its entirety.

Using the methodology of the present invention, chlorine dioxide will typically be generated over a period of about 15–30 minutes with some agitation. However, if the agitation is too great, the efficiency of the reaction can be greatly decreased, and not all of the metal chlorite may be converted to chlorine dioxide. The reason being, a localized lower pH is required at the point of reaction between the metal chlorite and the acid-forming compound. Too much agitation can lead to dispersion of the acid-forming compound and therefore a higher pH at the reaction site. Agitation will therefore not be necessary throughout the whole 15–30 minute period.

Chlorine dioxide provides an immediate and quite effective antimicrobial action against those contagious mastitis causing pathogens found on the teat when the composition of the present invention is applied. Chlorine dioxide rapidly vaporizes from the surface of the teat, however, and therefore does not provide long-lasting antimicrobial activity. Furthermore, should chlorine dioxide remain on the teat for an extended period of time, tissue irritation would occur.

It is therefore desirable, and quite beneficial, to provide a secondary antimicrobial agent for longer lasting residual antimicrobial activity. Such secondary antimicrobial agents useful herein include medium chain fatty acids. These acids typically have a carbon chain from about 2 to about 15 carbon atoms, and preferably from about 6 to about 12 carbon atoms. Such fatty acids include acetic, propionic, octanoic, heptanoic, decanoic, nonanoic (pelargonic), undecanoic, and so forth. Octanoic and heptanoic are preferable fatty acids. These acids are useful in amounts of about 0.1% to about 10% by weight of the total composition, and preferably from about 0.2% to about 2% by weight of the total composition.

Longer chain length fatty acids, e.g. $C_{11}$ to $C_{15}$, are typically solid at room temperature, and are more difficult to solubilize in the aqueous system. It may therefore be necessary to use a co-coupling agent or hydrotrope in order to solubilize the longer chain fatty acid. Shorter chain fatty acids can function to increase the solubility of a longer chain fatty acid. For instance, acetic acid and propionic acid may be used for such a purpose.

Heptanoic and octanoic acids have been found to have better residual antimicrobial activity than some other fatty acids. The fatty acids disrupt the metabolism of a cell by entering the cell membrane and interfering with the cell function. The fatty acid must therefore be able to cross the hydrophobic membrane of the cell. If the number of carbon atoms in the fatty acid chain is too low, the fatty acid is not hydrophobic enough. If the number of carbon atoms is too high, the fatty acid is not soluble in water. The fatty acid therefore loses efficacy.

The solid chlorine dioxide generating component of the present invention may, in addition to the acid-forming-forming compound and the metal chlorite, also contain the antimicrobial fatty acid in a solid form. For instance, some fatty acids, in particular those having a carbon chain length of 8 or lower, are in a naturally liquid state at ambient temperatures, whereas fatty acids having a chain length of greater than about 12 are in a naturally solid state at ambient temperatures. Those fatty acids in a naturally solid state are easily packaged with the metal chlorite and the acid-forming compound in the solid component. However, longer chain length fatty acids may require co-coupling agents or hydrotropes in order to solubilize the longer chain fatty acid into the system. Longer chain fatty acids may also be modified to improve the solubility.

If the fatty acid is a liquid, an absorbent may be used in order to provide a tablet with a layered or sandwich type of structure.

The pH of the mixture of the present invention is preferably from about 5 to about 10, more preferably from about 5.5 to about 10, and most preferably from about 5.5 to about 8. The neutral pH of the present invention provides a composition which exhibits less irritation to the skin of animals or humans.

Other ingredients may be optionally added to the compositions of the present invention including wetting agents (i.e. emulsifiers or surfactants), emulsion stabilizers, defoamers, buffers, other antimicrobial agents, fungicides, emollients (skin conditioning or moisturizing agents), hydrotropes, humectants, thickeners or rheology modifiers, preservatives, dyes, plasticizers, vitamin E, insect repellents, perfumes, and so forth. An ingredient such as a dye may be added to the composition at the time of use as a separate tablet form, for instance.

Wetting agents or surfactants are often used to provide wetting properties to insure complete contact between the surface to be disinfected and the use solution. Wetting agents or surfactants useful herein include linear alcohol alkoxylates, i.e. linear alcohol ethoxylate, nonylphenoxypolyethoxy ethanol, sodium dioctylsulfosuccinate such as Aerosol® TO-75 available from American Cyanamid Co./Industrial Chemical Division. Surfactants are useful up to about 2% by weight of the composition, and preferably up to about 0.5% by weight of the composition.

Emollients useful herein include but are not limited to propylene glycol, glycerin, lanolin or lanolin derivatives, sorbitol, polyethylene glycol, aloe vera, and so forth. These agents are useful to maintain a healthy teat skin and to counteract any potential irritation effect from formulation ingredients or from the environment. Emollients are useful up to about 15% by weight of the composition. The amount of emollient utilized in the compositions of the present invention may be reduced because the of the mildness of the pH of the final composition, i.e. 5–10.

Polymeric thickeners or rheology modifiers may be optionally added to the compositions of the present invention to allow for better adhesion to the surface of the teat. This is important to improve the residence time of the antimicrobial in contact with the pathogens. Furthermore, it decreases the amount of waste lost in terms of the composition "dripping" from the teat. Rheology modifiers may be inorganic or organic, and they may be water soluble or water dispersible. Organic thickeners may be divided into natural and synthetic polymers. Synthetic polymers may be natural based, or they may be petroleum based. These thickeners are useful up to about 1% by weight of the composition, and preferably up to about 0.5% by weight of the composition.

Inorganic thickeners include colloidal magnesium, aluminum silicates such as those sold under the tradename of Veegum®, colloidal clays such as those sold under the tradename of Bentonite®, silicas such as the Cab-o-sil® line, and so forth. These thickeners, sometimes referred to as fillers, may be fumed or precipitated to create particles with large surface to size ratios.

Natural hydrogel thickeners are those that are primarily derived from vegetable extrudates. For instance tragacanth, karaya and acacia gums; extractives including caragheenan, locust bean gum, guar gum, pectin and so forth; pure cultured fermentation products such as xanthan gum; and so forth.

Specific examples of useful rheology modifiers include xanthan gum, such as Kelzan® T available from and Keltrol® available from Kelco (Div. of Monsanto Company), and partially or fully hydrolyzed polyvinyl alcohol compositions. These materials are susceptible to shear stress wherein viscosity is reduced upon the addition of shear, and upon removal of the shear forces, the viscosity recovers. For teat dip compositions, the viscosity increases upon dipping, and upon removal, the viscosity returns, thereby immobilizing the coating on the teat so that little is wasted through drippage.

The rheology modifier may be a film former itself, or it may act cooperatively with a film-forming agent. For instance, xanthan gum may function both as a film former and as a rheology modifier, and partially or fully hydrolyzed polyvinyl alcohol may function both as a film-former, and as a rheology modifier. Film-forming agents are used in the barrier type teat dips.

Film-forming provides the formation of a barrier over the teat orifice in order to prevent access to the teat canal by the mastitis causing microorganisms. This barrier provides protection from the mastitis causing agents during the inter-milking periods.

Useful classes of film forming agents include natural hydrogels (i.e. natural gums), gelatin, vinyl polymers, cellulose based film formers including ethylhydroxyethyl cellulose, and so forth. Film formers are useful from 0% to about 10% by weight of the total composition, and preferably from about 0.01% to about 8% by weight of the total composition.

The above ingredients may be included in the aqueous component in solution, or they may be included in the solid component, but it is preferable to include these ingredients in the aqueous solution. However, the present invention may also comprise a system of several tablets, each having various ingredients, that are placed in water at the time of use.

The compositions of the present invention are useful as teat dips including predips, prepost dips and barrier dips.

Other applications in which the compositions of the present invention find use include liquid and solid drain santizers, carcass dips (e.g., those used at rendering facilities), hoof treatment compositions, antimicrobial lubricants, surgical scrubbing compositions and antimicrobial hand products, topical skin treatments, antimicrobial veterinarian products, body fluid spill disinfection compositions, high level disinfectants for invasive and non-invasive surgical instruments, and so forth.

EXAMPLES

The following base composition was prepared using standard mixing procedures.

TABLE I

| Ingredient | BS I | BS II | Description |
| --- | --- | --- | --- |
| 1) Deionized water | 86.27 | 85.27 | carrier |
| 2) Sodium hydroxide | 0.13 | 0.13 | buffer/counterion |
| 3) Xanthan Gum, Kelzan ® T | 0.10 | 0.10 | rheology modifier |
| 4) Polyvinyl pyrrolidone | 0.20 | 0.20 | anti-irritant |
| 5) Propylene glycol | 12.0 | 12.0 | humectant/emollient |
| 6) Lactic acid (food grade, 88%) | 0.60 | 0.60 | protic acid |
| 7) Heptanoic acid | 1.0 | — | antimicrobial |

TABLE I-continued

| Ingredient | BS I | BS II | Description |
|---|---|---|---|
| 8) Linear alcohol ethoxylate (9 moles ethylene oxide) | 0.10 | 0.10 | surfactant |
| 9) Dye | q.s. | q.s. | colorant |

Examples 1, 2 and 3 and Comparative Examples A, B and C

This experiment was used to determine what affect the addition of a fatty acid, the secondary antimicrobial agent, had on the effectiveness of the compositions in killing $E.$ $Coli$ and $S.$ $Aureus$. The secondary fatty acid used was heptanoic acid at a level of 1% in examples 1, 2 and 3. The comparative examples, A, B and C, contained no fatty acid.

Two base solutions, I and II, were prepared using the following mixing procedure. Ingredients 1 and 2 were added together in a mixing container. The agitator was turned on and ingredient 3 was slowly added to disperse evenly and smoothly throughout the mixture, without clumping together. The resultant combination was mixed until everything was thoroughly dissolved. Ingredient 4 was slowly added to obtain good dispersion, and the ingredients were mixed until everything was thoroughly dissolved. Ingredients 5, 6, 7, 8 and 9 were added slowly in order to enhance rapid dissolution without the ingredients concentrating at the bottom of the tank. The resultant combination was mixed for 10 minutes. Base solution II lacks ingredient 7, the heptanoic acid antimicrobial.

Sodium chlorite was then added to each of the base compositions, I and II, shown in Table I in varying amounts. Three compositions were prepared from each base solution. Sodium chlorite was added in amounts that were sufficient to form compositions having 200 ppm, 300 ppm and 400 ppm $ClO_2$. Six compositions were prepared in all.

The compositions were then tested for the antimicrobial effect against $Staphylococcus$ $aureus$ and $Escherichia$ $coli$. The inoculum numbers in CFU/mL were $1.1 \times 10^7$ (ATCC 6538) and $1.0 \times 10^8$ (ATCC 11229). The test temperature was 25° C. and the solution pH was 5.5. The following Table II illustrates the results obtained.

TABLE II

| Example | Exposure Time (seconds) | Log Reduction E. coli | Log Reduction S. Aureus |
|---|---|---|---|
| A | 15 | 0.15 | 0.12 |
| 200 ppm ClO₂ | 30 | 0.12 | 0.12 |
| B | 15 | >7.0 | >7.04 |
| 300 ppm ClO₂ | 30 | >7.0 | >7.04 |
| C | 15 | >7.0 | >7.04 |
| 400 ppm ClO₂ | 30 | >7.0 | >7.04 |
| 1 | 15 | >7.0 | 1.86 |
| 200 ppm ClO₂ and 1% heptanoic acid | 30 | >7.0 | 3.90 |
| 2 | 15 | >7.0 | >7.04 |
| 300 ppm ClO₂ and 1% heptanoic acid | 30 | >7.0 | >7.04 |
| 3 | 15 | >7.0 | >7.04 |
| 400 ppm ClO₂ and 1% heptanoic acid | 30 | >7.0 | >7.04 |

Comparative examples A, B and C were used to determine what concentration level of chlorine dioxide provided an effective antimicrobial kill of $E.$ $Coli$ and $S.$ $Aureus$. This level was determined to be 300 ppm with no secondary antimicrobial fatty acid added.

Examples 1, 2 and 3 additionally contained 1% heptanoic fatty acid as a secondary antimicrobial agent. As can be from the results found in Table II, the addition of acid provided a much beter antimicrobial kill at the lower level of chlorine dioxide, i.e. 200 ppm $ClO_2$, than the same composition, Comparative A, without any fatty acid. In fact, the sam level of kill was provided for $E.$ $Coli$ at 200 ppm $ClO_2$ and 1% fatty acid, as with those composition having 300 ppm and 400 ppm $ClO_2$ and no fatty acid.

The kill of $S.$ $Aureus$ is greatly improved with the addition of 1% fatty acid at 200 ppm $ClO_2$ concentration level over the same composition with no fatty acid. However, $S.$ $Aureus$ is more difficult to kill than $E.$ $Coli$ and consequently, the same level of kill is not exhibited for $S.$ $Aureus$ as for $E.$ $Coli$. This level of kill is acceptable, however.

Examples 4, 5 and 6 and Comparative D

The effect of various acids on the antimicrobial activity of the base solution was measured. No chlorine dioxide was added to the compositions. Acids were added to each sample at a concentration of 1%. Example 4 had 1% heptanoic acid and Comparative Example D had 1% lactic acid. Examples 5 and 6 utilized blends of acids. The antimicrobial activity of each was measured and compared in the following Table III.

TABLE III

| Example | Exposure Time minutes | Log Reduction E. coli | Log Reduction S. aureus |
|---|---|---|---|
| 4 | 5 | >7.11 | >7.54 |
| 1% heptanoic | 30 | >7.11 | >7.54 |
| D | 5 | 0.35 | 0.70 |
| 1% lactic | 30 | 0.34 | 0.75 |
| 5 | 5 | >7.11 | 6.16 |
| 0.67% heptanoic and 0.33% lactic | 30 | >7.11 | >7.54 |
| 6 | 5 | >7.11 | >7.54 |
| 0.67% heptanoic and 0.33% octanoic | 30 | >7.11 | >7.54 |

The results shown in Table III illustrate the antimicrobial effect of the medium chain fatty acids versus a protic acid, lactic acid, that is commonly utilized in teat dips. Comparative Example D, having only lactic acid, exhibited much lower antimicrobial activity.

Additionally, a longer exposure time is achieved with the fatty acid residual antimicrobial agent versus the lactic acid. The lactic acid used alone at 1% does not have much of any effect against the microbes. Substituting some of the heptanoic acid with lactic acid resulted in reduced kill. Using either heptanoic acid, or a heptanoic acid/octanoic acid blend resulted in improved kill over lactic acid or heptanoic acid/lactic acid blend. The octanoic acid has a potency against the microbes that is similar to heptanoic acid.

What is claimed is:

1. A two-part composition activatable to form an antimicrobial composition, which two parts when mixed result in an antimicrobial composition that has a pH in the range of about 5.0 to about 8 and contains from about 1 to 500 ppm chlorine dioxide, the two-part composition comprising:

Part a) a chlorine dioxide generating component in solid form comprising at least one acid-forming compound and at least one metal chlorite in a neutral solid carrier; and Part b) an aqueous component comprising an antimicrobial fatty acid having from about 6 to about 12 carbon atoms;

wherein the acid-forming compound has a pKa less than the antimicrobial fatty acid.

2. The composition of claim 1 wherein said pH of said antimicrobial composition is from about 5.2 to about 8.

3. The composition of claim 1 wherein the pKa of said acid-forming compound is less than about 4.5.

4. The composition of claim 1 wherein said at least one metal chlorite and said at least one acid-forming compound are in a pressed tablet form.

5. The composition of claim 1 wherein said at least one metal chlorite and said at least one acid-forming compound are in a powder form.

6. The composition of claim 5 wherein said at least one metal chlorite and said at least one acid-forming compound are separated from any other components by a membrane.

7. The composition of claim 1 wherein said solid carrier is selected from the group consisting of water insoluble compounds, water sensitive compounds, water soluble compounds and mixtures thereof.

8. The composition of claim 7 wherein said solid carrier is selected from the group consisting of polyolefins, copolymers of polyolefins, cellulose based materials, gelatins, vinylic polymers, and mixtures thereof.

9. The composition of claim 1 further comprising a dye in a solid form.

10. The composition of claim 1 wherein said acid-forming compound is a protic acid.

11. The composition of claim 1 wherein said acid-forming compound is a carboxylic acid.

12. The composition of claim 10 wherein said protic acid is selected from the group consisting of hydrochloric, sulfuric, sulfamic, nitric, phosphoric, citric, tartaric, boric, lactic, and mixtures thereof.

13. The composition of claim 1 wherein said fatty acid is selected from the group consisting of heptanoic and octanoic.

14. The composition of claim 1 wherein said composition further comprises from 0.01% to about 10% by weight of at least one film-former.

15. The composition of claim 1 wherein said chlorine dioxide concentration is measured at about 15 minutes to about 30 minutes after mixing said chlorine dioxide generating component and said aqueous component.

16. The composition of claim 1 wherein said antimicrobial fatty acid is present at a concentration from about 0.1% to about 2% by weight of the total composition.

17. The composition of claim 1 wherein said acid-forming compound is a protic acid; and said components a) and b) when mixed, providing a pH in the range of about 5 to about 8.

18. A two-part composition activatable to form an antimicrobial composition, which two parts when mixed result in an antimicrobial composition that has a pH in the range of about 5.0 to about 8 and contains from about 1 to 500 ppm chlorine dioxide, the two-part composition comprising:

Part a) a chlorine dioxide generating component in solid form comprising at least one acid-forming compound and at least one metal chlorite in a neutral solid carrier selected from the group consisting of aluminum silicate clays, bentonite, kaolin, attapulgite, halloysite, polyorganosilicates, micas, talcs and zeolites; and Part b) an aqueous component comprising an antimicrobial fatty acid having from about 6 to about 12 carbon atoms;

wherein the acid-forming compound has a pKa that is less than the pKa of the antimicrobial fatty acid.

* * * * *